United States Patent [19]

Kella

[11] 4,170,991
[45] Oct. 16, 1979

[54] SEAT BIB

[76] Inventor: Harry Y. Kella, 6316 Mesita Dr., San Diego, Calif. 92115

[21] Appl. No.: 795,516

[22] Filed: May 10, 1977

[51] Int. Cl.² ............................................. A61F 5/37
[52] U.S. Cl. ................................ 128/134; 128/287; 297/467; 297/485
[58] Field of Search ............... 128/134, 287; 297/354, 297/355, DIG. 4, 384, 385

[56] References Cited

U.S. PATENT DOCUMENTS

| | | | |
|---|---|---|---|
| 1,376,625 | 5/1921 | Johnston | 128/134 X |
| 2,170,703 | 8/1939 | Wayman et al. | 128/134 X |
| 2,827,898 | 3/1958 | Thompson | 128/134 |
| 3,162,196 | 12/1964 | Salk | 128/287 |
| 3,276,432 | 10/1966 | Murcott | 128/134 X |

*Primary Examiner*—Robert W. Michell
*Assistant Examiner*—M. A. Juten
*Attorney, Agent, or Firm*—Knox & Knox

[57] ABSTRACT

An accessory for a wheel chair for use by a patient seated therein and essentially a bib having a panel covering the chest and abdomen, a panel upon which the patient sits and a reduced crotch panel joining the other panels, with an absorbent pad covering the crotch panel and a unique adjustable belt to fasten the bib to the lateral upright members of the wheel chair, above the back rest of the chair, and quick attachment means for the rear lower end of the bib for connection to the standard rearwardly extending stub elements of the wheel chair frame used as pedals by attendants in tipping up the front of the wheel chair, the item being an effective patient supporting and restraining means.

3 Claims, 3 Drawing Figures

SEAT BIB

BACKGROUND OF THE INVENTION

Patients in wheel chairs frequently require means to support and/or restrain them against inadvertent falling or sliding out of the chair as, for example, when they fall asleep or try to lean too far from the upright seated position. Positive restraint is sometimes desirable. The commonest current method appears to be the use of bed sheets tied about the patient and this is obviously unattractive and awkward and sometimes ineffective. The prior art includes various bib structures, none of which is known to have been generally accepted, the closest patents known being U.S. Pat. No. 2,170,703 which is represented as being for tieing an infant in a high chair, this being accomplished by a bib with armholes and an aperture through which the legs of the child are extended, in addition to a crotch strap, and U.S. Pat. No. 2,851,033 which shows a bib covering the front of a patient and provided with straps fastened around the back of the wheel chair and "underneath the (seat) chair", this arrangement not positively preventing the patient from accidentially or deliberately slumping down and sliding forwardly. There is a need, therefore, for a simple, safe wheel chair accessory which will positively retain a patient in reasonable comfort and which can be very easily positioned and which will also incorporate the function of a diaper-like pad.

SUMMARY OF THE INVENTION

As claimed, the present invention represents an adequate response to the immediately abovementioned need, comprising a seat bib, so-called because it is in part sat upon and in part similar to an ordinary bib, the seat panel and the front panel being joined together by a padded crotch panel of reduced width to present a single elongated structure with attachment means at the ends thereof whereby the front panel can be strapped around the back of the chair above the back rest proper by a unique multiple-loop single buckle adjustable strap, and the seat panel has special loop straps which adjustably engage the pedal elements used by the attendants to tilt the wheel chair, the latter straps having bridles which prevent undue wrinkling of the seat panel.

DETAILED DESCRIPTION OF A PREFERRED EMBODIMENT

Figure 3:
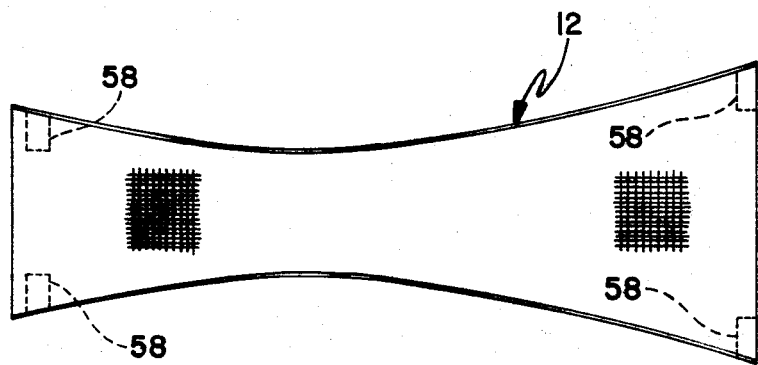
FIG. 3 is a plan view of the absorbent pad.

Referring now to the drawing wherein the numerals refer to like or identical elements in the different views, the seat bib is comprised of two principal parts, namely the seat bib proper, generally identified by the numeral 10 and the absorbent pad generally indicated at 12 and shown separately in FIG. 3.

The seat bib 10 is comprised of three panels which may be unitary, namely, the front panel 14, the crotch panel 16 and the seat panel 18. The front panel is so named because it is disposed in use to cover the front, that is, the chest and abdomen of a patient seated upright in a wheel chair somewhat diagrammatically illustrated at 20 in FIG. 1. The front panel 14 tapers from what may be considered the top edge 22 to its junction with the crotch panel 16. This top edge 22, like the entire periphery of the seat bib proper, is reinforced and finished by a hem 24 or by tape or the like stitched thereto as indicated at 26.

Figure 1:
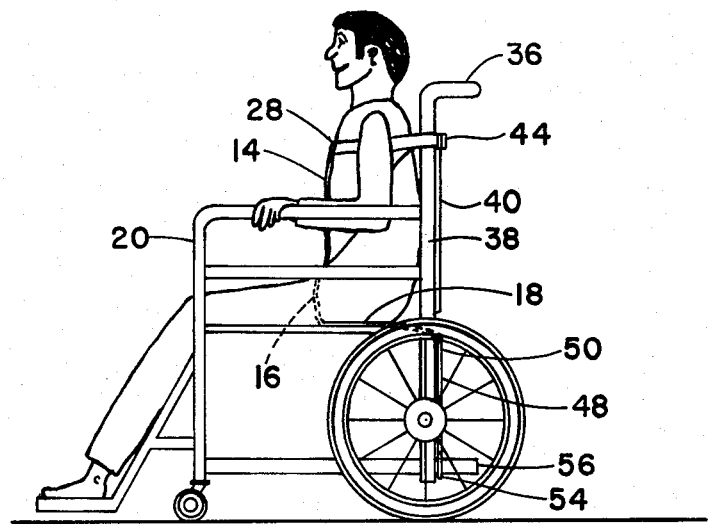
FIG. 1 is a side elevational view of an occupied wheel chair with the seat bib positioned as in normal use.
Figure 2:
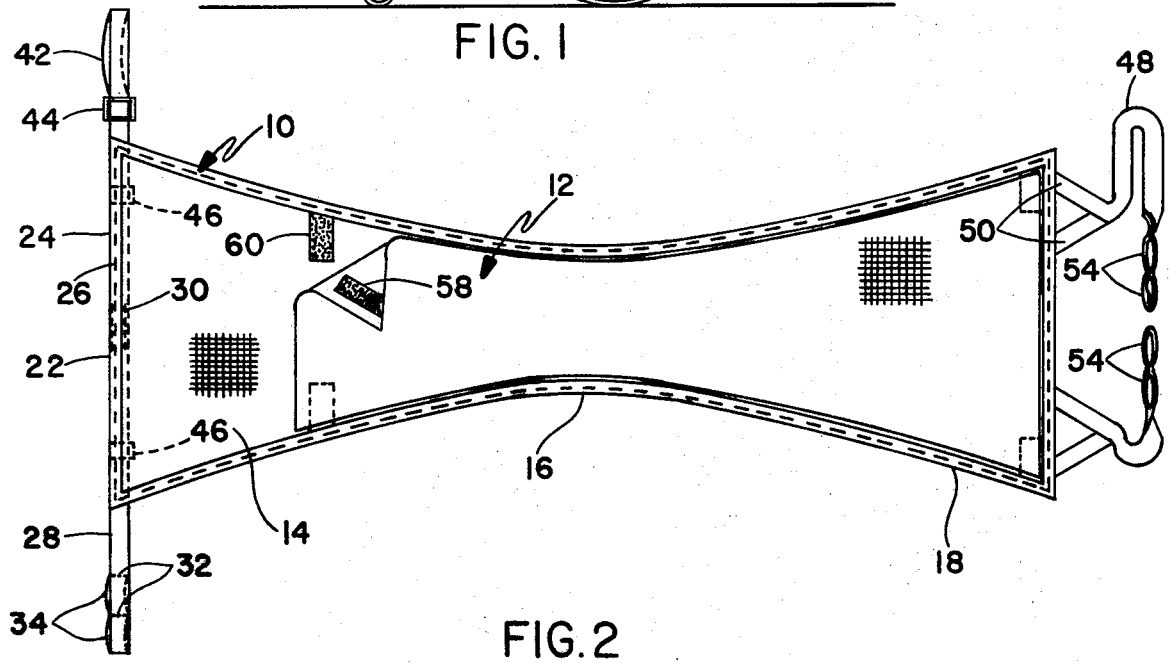
FIG. 2 is a plan view of the seat bib, extended and with the absorbent pad attached at three of the four attachment locations.

A unique adjustable belt 28 is also secured centrally of the top edge portion of the front panel as indicated by the stitching at 30 in FIG. 1. One end portion of the belt 28 is doubled back and stitched as at 32 at a plurality of spaced positions to provide open link portions 34 in the belt, so that a handle 36 of the wheel chair can be inserted into the open link portions selectively to permit adjustability of attachment of the belt at this end thereof. It will be understood that the open link portions are slid from the handle 36 down the corresponding upright lateral frame member 38 of the wheel chair and will in use be held close to the top of the member 38 by the back rest 40 of the chair.

The other end portion of 28 is also returned as indicated at 42 so that it may be similarly inserted over the corresponding handle, similar to the handle 36, on the opposite side of the chair and slid onto the corresponding upright lateral frame member, and adjustability in effective length at this end of the belt is accomplished by a fastener 44 which can be a simple slide buckle.

Belt loops 46, preferably only one on each side and positioned reasonably close to the outer edges of the front panel 14, complete the retention means for the front panel. These belt loops 46 permit limited sliding movement of the front panel relative to the virtually fixedly positioned belt and the central portion of the front panel and this greatly increases patient acceptance and comfort without unduly sacrificing the restraining function of the seat bib.

The crotch panel 16 as stated above may be unitary with the other panels and should be faired smoothly into both. This crotch panel is considerably reduced in width but should have very considerable width, on the order of six inches or more for adults, as some bunching and folding can be tolerated and is probably desirable.

Seat panel 18 may be variously shaped but in all cases should have a width at the distal end thereof comparable to the width of the front panel 14. It is desirable that the seat panel 18 should not bunch or wrinkle and the attachment straps 48 are constructed to achieve this function by having bifurcated portions or bridles 50 which transmit tension to four points 52 spaced along the distal end of the seat panel. The outer end portions of the straps 48 are each provided with open link portions 54 which are selectively inserted onto the rearwardly extending pedal elements 56 of the wheel chair which are used by the attendant in tipping up the front of the chair as in negotiating steps or curbs.

Finally, the soft absorbent pad 12 is attached over the crotch panel 16 and at least parts of the front and seat panels. This pad is dimensioned and configured to fit the underlying panel portions but need not reach upwardly past the midsection of the front panel. The pad and said underlying panel portions have inter-engaging fastening means of suitable character, such as inter-engaging elements sold under the trademark VELCRO as illustrated, and it is preferred that these fastening means be limited to placement near the four corners of the pad 12 as indicated at 58 and at corresponding positions on the front and seat pads as indicated typically at 60.

What I claim as new, and desire to secure by letters patent, is:

1. The combination of a wheel chair having a frame with a seat and including opposing upright members with a back rest therebetween and terminating in handles, and rearwardly extending pedal elements used in tipping the wheel chair, and a seat bib for use of a patient seated in the wheel chair, said bib comprising:
   (a) a front panel dimensioned and configured to extend over the chest and abdomen of the patient;
   (b) a seat panel, generally horizontally disposed in use, to extend over a portion of the seat under a patient;
   (c) a crotch panel of reduced width intermediate and joining said front and seat panels;
   (d) said front panel having means at the distal end thereof for attachment to a wheel chair comprising a belt secured thereto and having a plurality of open link portions spaced apart longitudinally of the belt at one end thereof, said link portions being capable of being selectively passed over one of the handles of the wheel chair so that said belt is adjustably positionable upon the corresponding one of the upright lateral members of the wheel chair above the back rest of the wheel chair, said belt having, on the other end portion thereof, a returned portion capable of being passed around the other of the upright members of the wheel chair, and means for adjusting the effective length of said other end portion; and
   (e) said seat panel having means for attachment of the distal end thereof to said wheel chair comprising a pair of straps, each strap having a plurality of integral loop portions spaced therealong, said loop portions being selectively engageable onto said rearwardly extending pedal elements used in tipping the wheel chair wherein said straps include branched bridle portions at the proximal ends thereof for more wrinkle-free deployment of said seat panel.

2. A seat bib according to claim 1 and including an absorbent pad dimensioned and configured to cover said crotch and seat panel and to reach upwardly to the midsection of said front panel; and means for easily removable attachment of said pad to said seat portion and to said midsection of the front panel.

3. A seat bib according to claim 1;
   said front panel being fixedly secured to said belt only at the center portion of said distal end of the front panel; and
   said front panel having belt loops through which said belt is threaded on each side of said center portion, whereby the lateral portions of said front panel have capability of limitd sliding adjustment on the belt even when said belt is firmly connected to said wheel chair.

* * * * *